United States Patent [19]
Hawkins et al.

[11] Patent Number: 5,597,392
[45] Date of Patent: Jan. 28, 1997

[54] REGISTER FILTER

[75] Inventors: Roger S. Hawkins, Waterford; Christopher N. Loridas, Clarkston, both of Mich.

[73] Assignee: Hawkins & Loridas, Inc., Troy, Mich.

[21] Appl. No.: 359,528

[22] Filed: Dec. 20, 1994

[51] Int. Cl.[6] .............................. A61L 9/00; B01D 29/11; B01D 35/02
[52] U.S. Cl. ..................... 55/274; 55/378; 55/DIG. 35; 422/123
[58] Field of Search .......................... 55/279, 274, 378, 55/DIG. 35; 422/120, 123

[56] References Cited

U.S. PATENT DOCUMENTS

| | | | |
|---|---|---|---|
| 3,005,516 | 10/1961 | Klein | 55/509 |
| 3,046,719 | 7/1962 | Tropiano | 55/417 |
| 3,408,438 | 10/1968 | Staunton | 264/252 |
| 3,693,327 | 9/1972 | Scheinberg | 55/274 |
| 3,768,235 | 10/1973 | Meyer et al. | 55/385.5 |
| 3,999,969 | 12/1976 | Shuler | 55/418 |
| 4,334,899 | 6/1982 | McConnell | 55/DIG. 35 |
| 4,689,058 | 8/1987 | Vogt et al. | 55/279 |
| 4,885,015 | 12/1989 | Goulet et al. | 55/497 |
| 4,961,849 | 10/1990 | Hull et al. | 210/169 |
| 5,100,445 | 3/1992 | Johnson et al. | 55/413 |
| 5,240,487 | 8/1993 | Kung | 55/486 |

*Primary Examiner*—Robert J. Warden
*Assistant Examiner*—Theresa T. Snider
*Attorney, Agent, or Firm*— Reising, Ethington, Barnard & Perry, LLP

[57] ABSTRACT

A filter assembly (10) adapted to be secured to a register (18) of the type used for covering a forced air duct outlet (12) in heating/cooling systems is disclosed. The filter assembly (10) removes contaminant particles from air flowing through the forced air duct outlet (12). The filter assembly (10) includes a filter material (33) of permeable and pliable material and an elastic band (34) secured to the filter material (33) for clamping the filter material (33) to the exterior surface (27) of the register skirt (26).

27 Claims, 2 Drawing Sheets

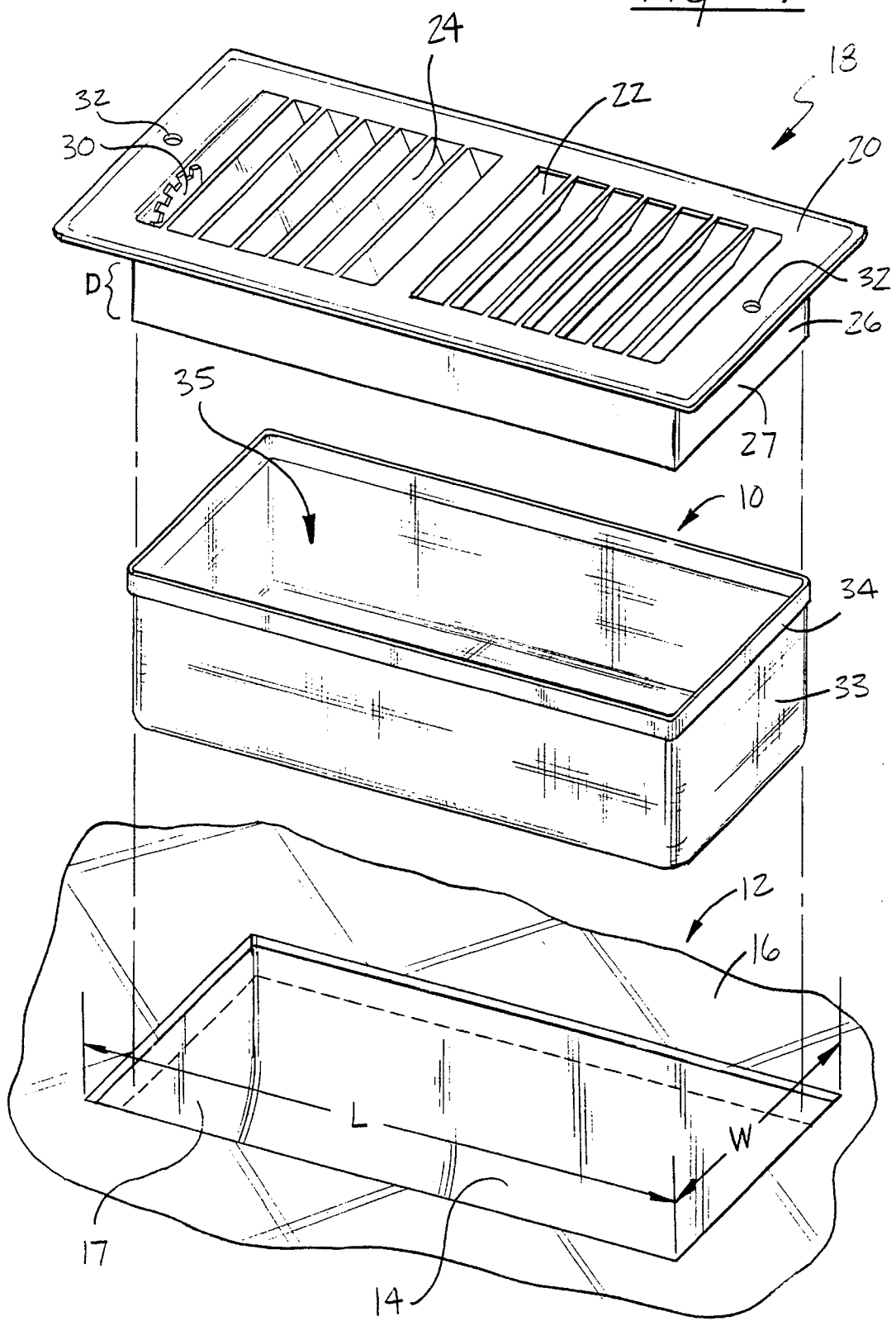

5,597,392

REGISTER FILTER

TECHNICAL FIELD

The subject invention relates to filter assemblies adapted to be secured to a register of the type used for covering a forced air duct outlet in heating/cooling systems.

BACKGROUND ART

Removal of contaminant particles from forced air heating/cooling systems is conventionally accomplished by a filter placed between a duct carrying air back to the heating/cooling system and the fan used to propel the air. However, these filters do not remove contaminant particles located between the heating/cooling system and the forced air duct outlet. For example, dust accumulates within the duct work extending between the heating/cooling system and the register covering a forced air duct outlet. In order to capture the dust and contaminant particles existing between the heating/cooling system and the air duct outlet, filter units have been positioned within a register which covers the forced air duct outlet. U.S. Pat. No. 5,240,487 to Kung discloses such a filter unit. The Kung '487 patent discloses a frame which supports an air filter wherein the frame is inserted into a forced air heating and/or cooling system duct adjacent to a duct outlet and within a floor or wall register. Specifically, the frame and air filter is friction fitted within the skirt of the register. The air filter comprises a two-ply fibrous sheet with an opening between the plies to receive the frame. A scent dispenser is mounted to the frame for containing scented air freshening material. The frame and filter unit of the Kung '487 patent has a number of disadvantages. The frame and filter unit requires complicated manufacturing methods and therefore is costly to manufacture. Also, the frame and air filter unit is a complicated structural arrangement for accomplishing a simple task. It is desirable to produce a register filter assembly having a simple structural arrangement which is easy to manufacture.

SUMMARY OF THE INVENTION AND ADVANTAGES

The present invention is a filter assembly for removing contaminant particles from air flowing through a forced air duct outlet wherein said filter assembly is adapted to be secured to a register of the type comprising a face plate having a vent, a plurality of vanes extending across the vent and a skirt having an interior surface and an exterior surface extending outwardly from the face plate. The filter assembly comprises a filter material and is characterized by clamping means for clamping the filter material to the exterior surface of the skirt.

The primary object and advantage of the present invention is to provide a filter assembly for removing dust and other contaminant particles transmitted from a forced air duct outlet through a register and into a room. It is desirable to remove contaminants such as dust, before they can enter the room. This minimizes the need to remove dust from the room. Another important object of the invention is to provide a filter assembly which is easily attachable to a register. A further object of the invention is to provide a filter assembly for a register which is simple to manufacture, has a simple structural design and uses cost advantageous material.

BRIEF DESCRIPTION OF THE DRAWINGS

FIG. 1 is an exploded view of the filter assembly of the present invention.

DESCRIPTION OF THE PREFERRED EMBODIMENT

Figure 3:
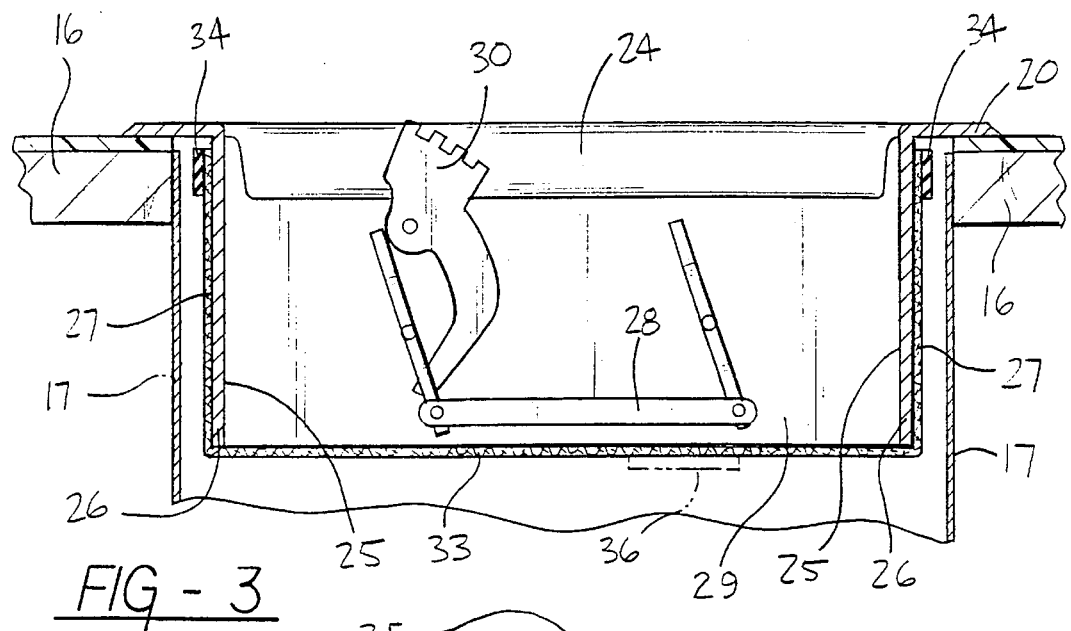
FIG. 3 is a cross sectional view of the filter assembly secured to the exterior surface of the register skirt with the register skirt and filter assembly disposed within the air duct outlet.

Referring to FIG. 1, the filter means or assembly 10 of the present invention is shown in its operating environment. A forced air duct outlet 12 of the type used in forced air heating/cooling systems is shown. Typically a forced air duct outlet 12 includes a rectangular hole 14 through a wall, floor, or ceiling 16. The hole 14 has a standard width W and a standard length L. The forced air duct outlet 12 further includes a rectangular duct 17 having a width W and a length L. The rectangular duct 17 is positioned to abut the longitudinal and latitudinal edges of the rectangular opening 14.

Figure 2:
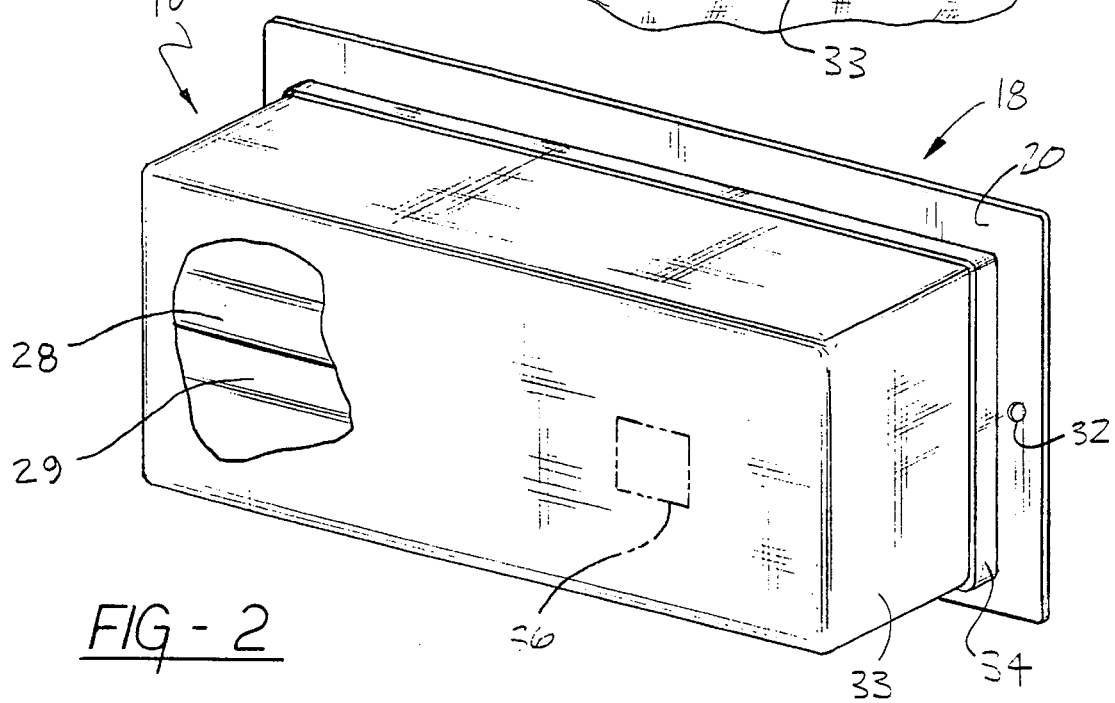
FIG. 2 is a rear perspective view of the filter assembly of the present invention secured to the register skirt with a cut-away in the filter assembly showing the register damper.

According to the present invention, a register 18 is provided for covering the forced air duct outlet 12. Referring to FIGS. 1–3, the register 18 comprises a rectangular face plate 20 having a register vent or opening 22 therein. The register 18 further comprises a plurality of vanes or louvers 24 extending across the vent 22 and fixed to the face plate 20. Alternatively, the vanes 24 can be movable so as to control the direction of air flowing out of the register 18. The register 18 further includes a rectangular skirt 26 extending perpendicularly outwardly from the face plate 20 for insertion into the forced air duct outlet 12 and, more specifically, into the hole 14 of the forced air duct outlet 12.

The skirt 26 has a length less than length L, a width less than width W, and a depth D so that the skirt 26 can fit snugly within the hole 14. The skirt 26 includes an interior surface 25 and an exterior surface 27 as best seen in FIGS. 1 and 2. The skirt forms an inlet 29 in fluid communication with vent 22. The rectangular face plate 20 has a length greater than L and a width greater than W so that the face plate 20 abuts against the wall, floor, or ceiling 16 when the skirt 26 is fully inserted within the hole 14.

The register 18 further may include a damper 28 for controlling the volume of air flowing through the vent 22 of the register 18. The damper 28 is movable between a plurality of open positions for allowing varying volumes of air to flow from the heating/cooling system, out of the air duct outlet 12 and through the vent 22 of the register 18 and a closed positioned for preventing the flow of air through the vent 22. Movement of the damper 28 is controlled by a rotatable lever 30. The face plate 20 includes holes 32 for mounting the face plate 20 to the wall, floor or ceiling 16.

According to the present invention, a filter means or assembly 10 is provided for removing contaminant particles, such as dust, from the air flowing between the heating/cooling system and the forced air duct outlet 12. The filter assembly 10 comprises a filter material 33 made from a permeable and pliable material. It is important that the filter material 33 have pores or openings large enough so as to not unduly restrict the flow of air therethrough, yet small enough to capture airborne contaminants, such as for example dust. One preferable filter material 33 comprises nylon of the type commonly used to make women's nylon stockings or hosiery. The weave of the nylon filter material 33 may be adjusted to adjust the pore size so as to maximize the advantage of the present invention. It will be appreciated that any type of filter medium may be used within the context of the present invention. By way of example only, other types of filter material that may be used are those commonly used in connection with dust masks.

Figure 4:
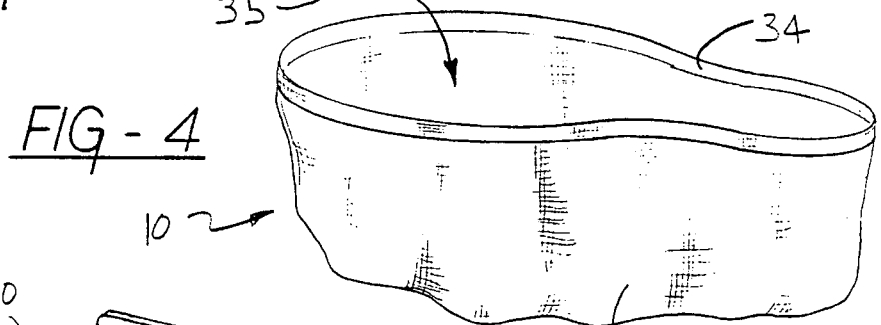
FIG. 4 is a perspective view of the filter assembly shown in its non-expanded sock-like shape.

The filter assembly 10 further comprises a clamping means 34 for clamping the filter material 33 to the exterior surface 27 of the skirt 26. The clamping means 34 includes a band 34. The band 34 can include a string, an adjustable belt or strap, a drawstring secured to the filter material 33, an elastic band 34, or any other type of band that is capable of securing the filter material 33 about the exterior of the skirt 26. The band 34 is preferably of the elastic type. The elastic band 34 is made from an elastic material such as, for example, rubber. The elastic band 34 is used to secure the filter material 33 to the exterior surface 27 of the skirt 26. As seen best in FIG. 3, the elastic band 34 is placed over the exterior surface 27 of the skirt 26 and is frictionally fitted or clamped thereto. In the preferred embodiment, the elastic band 34 is sewn or stitched to or otherwise attached to the periphery of the filter material 33 such that the filter material 33 takes on a tubular sock-like shape with one opening 35 therein (FIG. 4).

The filter assembly 10 fits about the exterior surface 27 of the skirt 26 and covers the inlet 29 formed by the skirt 26. That is, the filter assembly 10 is disposed outside the periphery of the skirt 26 and is secured by the elastic band. In other words, the skirt 26 is inserted into the opening 35 of the filter assembly 10. To insert the skirt 26 into the opening 35 the elastic band 34 must first be stretched, expanded, or deformed to increase the size of the opening 35 to fit around the skirt 26. Then, the elastic band 34 is allowed to resiliently grip the exterior surface 27 of the skirt 26. The filter material 33 then covers the inlet 29 to remove contaminants from the air flowing therethrough. Preferably the filter material 33 is taut over the opening when the filter material 33 is inserted about the skirt 26.

In operation, air flowing from the heating/cooling system and through the air duct outlet 12 must pass through the filter material 33 to exit the vent 22 of the register 18. The filter material 33 captures contaminant solid particles contained in the air flowing from the heating/cooling system. Because of the ease of attachment of the filter material 33 with the skirt 26, and the relatively inexpense of the current system, the filter material 33 can be cleaned or changed often.

The filter assembly 10 of the present invention can also include a carbon monoxide detector means 36 secured to the filter material 33 for detecting carbon monoxide flowing therethrough. The carbon monoxide detector means 36 can be of any commercially available type.

The filter assembly 10 also can include scent means secured to the filter material 33 for scenting air flowing therethrough. The scent means can comprise any scented material. The scented material is then dispensed into the room by the air passing through the filter. Preferably the carbon monoxide detector 36 and scented material are secured to the filter assembly 10 by using any conventional techniques such as stitch, VELCRO, or adhesive. Alternatively, the filter material 33 itself can be scented.

The filter assembly 10 shown is used in connection with a register 18 having a common rectangular face plate 20 and a rectangular skirt 26. It will be appreciated that any shape face plate 20 and/or skirt 26 can be utilized within the scope of the present invention.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. In combination with a register (18) for covering a forced air duct outlet (12) of the type used in heating/cooling systems utilizing air ducts wherein said register (18) comprises a face plate (20) having a vent (22) and a skirt (26) having an interior surface (25) and an exterior surface (27) extending outwardly from said face plate (20) for insertion into the forced air duct outlet (12), filter means (10) for disposition about said exterior surface (27) for removing contaminant particles from air flowing through the forced air duct outlet (12), said filter means (10) comprising:

a filter material (33); and clamping means (34) attached to said filter material (33) for securing said filter material (33) to said exterior surface (27) of said skirt (26).

2. The combination of claim 1 wherein said filter means (10) further comprises carbon monoxide detector means (36) for detecting carbon monoxide flowing therethrough.

3. The combination of claim 1 wherein said filter means (10) further comprises scent means for scenting air flowing therethrough.

4. The combination of claim 1 wherein said clamping means (34) comprises a band (34).

5. The combination of claim 4 wherein said band (34) is elastic.

6. The combination of claim 5 wherein said elastic band (34) is secured to said filter material (33).

7. The combination of claim 6 wherein said elastic band (34) is secured along the periphery of said filter material (33).

8. The combination of claim 7 wherein said filter means (10) has a tubular shape with an opening (35) therein.

9. The combination of claim 8 wherein said elastic band (34) comprises rubber.

10. The combination of claim 4 wherein said filter material (33) is permeable and pliable.

11. The combination of claim 10 wherein said filter material (33) comprises nylon.

12. In combination with a register (18) for covering a forced air duct outlet (12) of the type used in heating/cooling systems utilizing air ducts wherein said register (18) comprises a face plate (20) having a vent (22) and a skirt (26) having an interior surface (25) and an exterior surface (27) extending outwardly from said face plate (20) for insertion into the forced air duct outlet (12), filter means (10) for disposition about said exterior surface (27) for removing contaminant particles from air flowing through the forced air duct outlet (12), said filter means (10) comprising:

a permeable and pliable filter material (33); and a band (34) secured along the periphery of said filter material (33) to secure said filter material (33) to said exterior surface (27) of said skirt (26).

13. The combination of claim 12 wherein said filter means (10) further comprises carbon monoxide detector means (36) for detecting carbon monoxide flowing therethrough.

14. The combination of claim 12 wherein said filter means (10) further comprises scent means for scenting air flowing therethrough.

15. In combination with a register (18) for covering an air duct outlet (12) of the type used in heating/cooling systems utilizing air ducts wherein said register (18) is of the type comprising a face plate (20) having a vent (22) and a skirt (26) having an interior surface (25) and an exterior surface (27) extending outwardly from said face plate (20), a filter assembly (10) comprising:

a filter material (33); and a band (34) attached to said filter material (33) for securing said filter material (33) to said exterior surface (27) of said skirt (26).

16. The filter assembly (10) of claim 15 wherein said filter material (33) further comprises carbon monoxide detector means (36) for detecting carbon monoxide flowing therethrough.

17. The filter assembly (10) of claim 15 wherein said filter material (33) further comprises scent means for scenting air flowing therethrough.

18. The filter assembly (10) of claim 15 wherein said band (34) is elastic.

19. The filter assembly (10) of claim 18 wherein said elastic band (34) is secured to said filter material (33).

20. The filter assembly (10) of claim 19 wherein said elastic band (34) is secured along the periphery of said filter material (33).

21. The filter assembly (10) of claim 20 wherein said filter assembly (10) has a tubular shape with an opening (35) therein.

22. The filter assembly (10) of claim 21 wherein said elastic band (34) comprises rubber.

23. The filter assembly (10) of claim 15 wherein said filter material (33) is permeable and pliable.

24. The filter assembly (10) of claim 23 wherein said filter material comprises nylon.

25. In combination with a register (18) for covering an air duct outlet (12) of the type used in heating/cooling systems utilizing air ducts wherein said register (18) is of the type comprising a face plate (20) having a vent (22) and a skirt (26) having an interior surface (25) and an exterior surface (27) extending outwardly from said face plate (20), a filter assembly (10) comprising:

a permeable and pliable filter material (33); and a band (34) secured along the periphery of said filter material (33) to secure said filter material (33) to said exterior surface (27) of said skirt (26).

26. The filter assembly (10) of claim 25 further including a carbon monoxide detector (36) for detecting carbon monoxide flowing therethrough.

27. The filter assembly (10) of claim 25 further including scent means for scenting air flowing therethrough.

* * * * *